(12) United States Patent
Morrissey et al.

(10) Patent No.: US 8,556,497 B2
(45) Date of Patent: *Oct. 15, 2013

(54) PLASTIC BAG CONTAINING A DISPOSABLE VORTEX BREAKER

(75) Inventors: Martin Morrissey, Beverly, MA (US); David DeCoste, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/399,354

(22) Filed: Feb. 17, 2012

(65) Prior Publication Data

US 2012/0155216 A1 Jun. 21, 2012

(51) Int. Cl.
*B01F 13/08* (2006.01)

(52) U.S. Cl.
USPC .................. 366/273; 366/306; 366/307

(58) Field of Classification Search
USPC .......... 366/273, 274, 306, 307, 349; 604/416, 604/903; 215/DIG. 3, DIG. 8; 435/302.1; 416/3; 383/127; 206/219–221, 818
See application file for complete search history.

(56) References Cited

U.S. PATENT DOCUMENTS

| | | | |
|---|---|---|---|
| 3,647,397 A * | 3/1972 | Coleman ................... | 366/167.1 |
| 4,711,582 A * | 12/1987 | Kennedy ..................... | 366/279 |
| 5,533,804 A * | 7/1996 | Larsson et al. ............... | 366/274 |
| 5,676,462 A | 10/1997 | Fraczek et al. | |
| 5,803,137 A * | 9/1998 | Shimotoyodome et al. .... | 141/67 |
| 6,083,587 A | 7/2000 | Smith et al. | |
| 6,844,186 B2 * | 1/2005 | Carll ........................ | 435/289.1 |
| 7,153,021 B2 * | 12/2006 | Goodwin et al. ............. | 366/273 |
| 7,278,780 B2 * | 10/2007 | Goodwin et al. ............. | 366/273 |
| 7,547,135 B2 | 6/2009 | Kocienski | |
| 8,172,453 B2 * | 5/2012 | Boussemart et al. ......... | 366/145 |
| 2003/0077466 A1 | 4/2003 | Smith et al. | |
| 2007/0253287 A1 * | 11/2007 | Myhrberg et al. ............ | 366/273 |
| 2009/0314666 A1 * | 12/2009 | Reif et al. .................... | 206/221 |
| 2012/0155216 A1 * | 6/2012 | Morrissey et al. ............ | 366/273 |
| 2013/0121104 A1 * | 5/2013 | Castillo et al. ............... | 366/273 |

FOREIGN PATENT DOCUMENTS

| | | |
|---|---|---|
| DE | 273168 C | 4/1914 |
| DE | 575198 C | 4/1933 |

(Continued)

OTHER PUBLICATIONS

International Search Report and the Written Opinion for PCT Application No. PCT/US2011/043181 mailed on Sep. 14, 2011, 6 pages.

(Continued)

*Primary Examiner* — Charles E Cooley
(74) *Attorney, Agent, or Firm* — EMD Millipore Corporation

(57) ABSTRACT

The present invention consists of a closed presterilized bag having a disposable mixing element within it, a drive mechanism outside of the bag for rotating the mixing element without voiding sterility and a vortex breaker in the form of one or more plastic sheet materials that are attached to various inner surfaces of the bag and disrupt the formation of vortices within the bag. Preferably the sheet(s) are formed of the same material as the bag and are sealed to the bag surfaces. More preferably, the sheet(s) extend across a diameter of the bag. Most preferably, the sheet(s) are perforated with one or more slits or openings to allow for good flow and mixing without a vortex being formed.

17 Claims, 5 Drawing Sheets

(56) References Cited

FOREIGN PATENT DOCUMENTS

| | | |
|---|---|---|
| DE | 202007005868 U1 | 7/2007 |
| DE | 202007005884 U1 | 7/2007 |
| DE | 102009005962 A1 | 7/2010 |
| EP | 1369170 A2 | 12/2003 |
| EP | 1842800 A2 | 10/2007 |
| SU | 1669524 A1 | 8/1991 |

OTHER PUBLICATIONS

International Preliminary Report on Patentability for PCT Patent Application No. PCT/US2011/043181, mailed on Feb. 14, 2013, 8 pages.

* cited by examiner

PLASTIC BAG CONTAINING A DISPOSABLE VORTEX BREAKER

CROSS-REFERENCE TO RELATED APPLICATIONS

The present application is a Divisional Patent Application of U.S. patent application Ser. No. 13/178,097 filed on Jul. 7, 2011 which claims the benefit of U.S. Provisional Patent Application No. 61/369,249, filed on Jul. 30, 2010, the entire contents of which are incorporated by reference herein their entirety.

The present invention relates to a system that allows for vortex-free mixing. More particularly, it relates to a vortex breaker for mixing in a disposable plastic bag.

BACKGROUND OF THE INVENTION

In the biotech industry, companies mix various liquid, liquid/solid materials together such as cell culture media, buffers, reagents and other such materials as well as protein containing solutions. Typically this has been done in a steel vat or tank with the amounts of materials such as powder and liquid added in controlled amounts. A mixer such as a magnetically driven stainless steel mixer such as the Novaseptic® mixer from Millipore or a shaft driven mixer such as Lightnin® mixers available from SPX Corporation can be used. Additional supplements in liquid or powder form can also be added in the same mixing or in a subsequent mixing step(s). Once the solution is prepared it is filtered and may be used directly or sealed in sterile containers for future use.

To be safe, the solutions must be pure and sterile. Therefore, the equipment must be thoroughly cleaned such as with a sodium hydroxide generally 1 M) solution and sterilized with steam between uses to ensure that no cross over material from the last mixing batch and no bacteria, mold or fungus from the environment is in the tank before a new batch is mixed. This cleaning and sterilizing process is labor intensive, time consuming, costly and often requires the partial disassembly of one or more components of the system and their reassembly afterward An alternative has been to use a closed, presterilized plastic mixing bag and disposable mixing component such as is described in U.S. Pat. No. 7,278,780. However, it has issues with creating a vortex during mixing unless operated at slow speeds. Either alternative is undesirable. A vortex leads to inefficient mixing and therefore requires a large amount of additional time to ensure that the mixing is complete. In addition with protein containing streams, the vortex entrains air which has adverse effects on the proteins including oxidation and shear as will be explained below. The alternative, to mix at a speed below the vortex creation is also unacceptable as it too requires additional time and may never achieve suitable mixing results.

U.S. Pat. No. 7,547,135 suggests adding rigid baffles vertically along the interior wall of a rigid molded plastic container to reduce vortex formation and increase mixing efficiency. However, the handling and shipment of a large molded structure (up to 1000 or 2000 liters capacity) is inefficient as is the storage of such containers.

While it is desired to add rigid baffles to the sides of the container this has proven to be difficult. The baffles can adversely affect the ability to fold the bag for compact shipping. Additionally, they can rupture the bag when and where they the bag surface during transportation and shipping.

What is needed is a disposable container for mixing that has the advantages of the bag with the baffle/vortex inhibiting effect of the rigid baffles to enable simple and efficient mixing.

SUMMARY OF THE INVENTION

The present invention consists of a closed presterilized bag having a disposable mixing element within it, a drive mechanism outside of the bag for rotating the mixing element without voiding sterility and a vortex breaker in the form of one or more plastic sheet materials that are attached to various inner surfaces of the bag and disrupt the formation of vortices within the bag. Preferably the sheet(s) are formed of the same material as the bag and are sealed to the bag surfaces. More preferably, the sheet(s) extend across a diameter of the bag. Most preferably, the sheet(s) are perforated with one or more slits or openings to allow for good flow and mixing without a vortex being formed.

It is an object of the present invention to provide a disposable mixer comprising a plastic bag having a bottom, one or more substantially vertical sides each having a lower portion attached to the bottom and a top connected an upper portion of the one or more vertical sides, the bag having an internal volume defined by the inner surfaces of the bottom, one or more sides and top, a disposable mixer contained within the internal volume of the bag and one or more vortex breakers formed of sheet of plastic material attached to a surface selected from the group Consisting of the bottom, a side and the top of the bag and extending to a surface selected from the group consisting of the bottom, a side and the top of the bag.

It is another object of the present invention to provide a sheet that extends from a first side of the bag to a second side of the bag.

It is a further object of the present invention to provide the sheet extending from a first side of the bag to a second side of the bag and the sheet contains one or more openings in the sheet.

It is another object of the present invention to provide the sheet extends from the bottom of the bag to a side of the bag.

It is an additional object of the present invention to provide the sheet extends from the bottom of the bag to a side of the bag and the sheet contains one or more openings in the sheet.

It is another object of the present invention to provide the sheet extends from the bottom of the bag to the top of the bag.

It is another object of the present invention to provide the sheet extends from the bottom of the bag to the top of the bag and the sheet contains one or more openings in the sheet.

It is another object of the present invention to provide the mixer is selected from the group consisting of magnetic stir bars, magnetically driven mixers and shaft driven mixers having the shaft extending into the interior volume of the bag form a surface selected from the top and the bottom.

It is another object of the present invention to provide the mixer is magnetically driver mixer located in the bottom of the bag.

It is another object of the present invention to provide a plastic bag having a bottom, one or more substantially vertical sides each having a lower portion attached to the bottom and a top connected an upper portion of the one or more vertical sides, the bag having an internal volume defined by the inner surfaces of the bottom, one or more sides and top, a magnetically driven disposable mixer mounted to the bottom of the bag and contained within the internal volume of the bag and one or more vortex breakers formed of sheet of plastic material attached to a first side surface of the bag to a second side surface of the bag.

It is another object of the present invention to provide the sheet extends from the first side surface to the second side surface in a substantially horizontal manner.

It is another object of the present invention to provide the sheet extends from the first side surface to the second side surface along a diameter of a cross section of the interior volume of the bag.

It is another object of the present invention to provide the sheet extends from the first side surface to the second side surface along a diameter of a cross section of the interior volume of the bag and the sheet contains one or more openings.

It is another object of the present invention to provide the sheet extends from the first side surface to the second side surface in a substantially horizontal manner and the sheet contains one or more openings.

It is another object of the present invention to provide two or more vertical sides and sheet extends from the first side surface to the second side surface in a substantially horizontal manner and the sheet contains one or more openings.

It is another object of the present invention to provide two or more vertical sides and the two or more vertical sides are secured to each other along a series of vertical seams and wherein the sheet is secured to and extends from a seam of the first side to a seam of the second side surface in a substantially horizontal manner and the sheet contains one or more openings.

It is another object of the present invention to provide the sheet extends at least partially through the interior volume vertically.

It is another object of the present invention to provide the sheet with a height at least 5% of the height of the vertical sides of the bag above the impellers on the mixing device.

It is another object of the present invention to provide the sheet spaced apart from the top of the mixing device.

It is another object of the present invention to provide a second sheet extending between two inner surfaces of the vertical side wall(s) and wherein the second sheet is at an angle to a plane of the first sheet defined as the direction from the first side surface to the second side surface of the bag.

It is another object of the present invention to provide the mixer comprises a stirring rod with one or more paddles and the sheet has an opening formed in the sheet to allow the rod to extend through the sheet.

It is a further embodiment of the present invention to provide a sheet that when the bag is unfilled is not under tension and when the bag is filled is under tension.

IN THE DRAWINGS

DETAILED SPECIFICATION

The present invention relates to a disposable mixing system that allows one to mix various suspended components together and/or otherwise mix solutions without vortex formation and without the need for cleaning and sterilization in between batches. The system can be used in association with cell culture media preparation, buffer preparation, reagents and other materials and solutions used in the biotech industry and can also be used with a vast array of other solutions outside of the biotech industry such as juice or food applications, paints and the like. Preferably it is used with protein containing solutions as a vortex can have adverse effects on the proteins. A vortex entrains air into the process fluid. Air in a process fluid is bad for the proteins as it degrade proteins by oxidation, the air bubbles have high surface tensions which induces stress on the proteins on the air bubble surface and when entrained, air bubbles are pulled into the pump, there the bubbles implode and degrade/denature the proteins by the shear created by the implosion and pump action.

Figure 1:
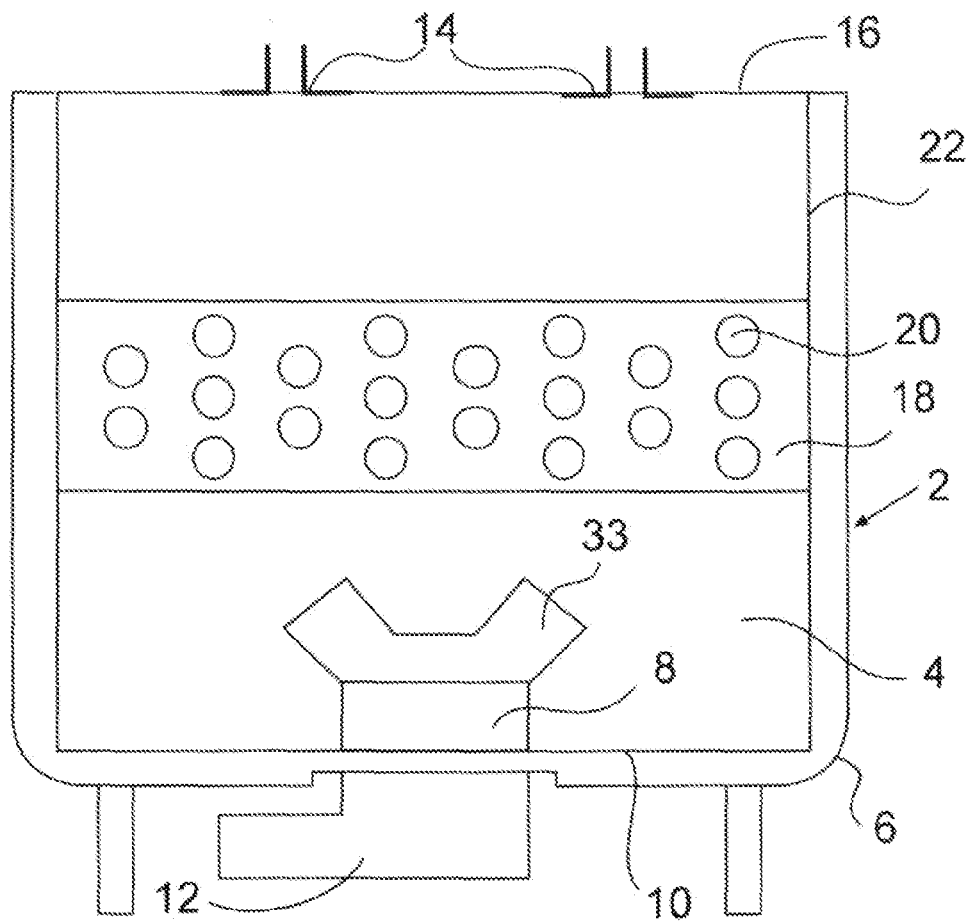
FIG. 1 shows a first embodiment of the present invention in cross-sectional view.

As shown in FIG. 1 the mixing system 2 is a plastic bag 4 preferably contained within a rigid reusable container 6. This container 6 can be made of metal such as stainless steel, plastic such as polyethylene or polypropylene, fiberglass composites, carbon composites and the like. One such holder is known as the Mobius® mix system available from Millipore Corporation.

The bag 4 has a magnetic mixing element 8 disposed within it preferably at or near the bottom 10 of the bag 4. Disposed below the container 6 and the bag 4 adjacent the mixing element 8 is a magnetic drive 12. This allows the element 8 with impellers 33 to be isolated and kept sterile within the bag 4 while being driven by the external drive 12 through magnetic coupling of the element 8 and the drive 12. One or more ports 14 (in this example 2 ports) can be located in the bag 4 and sealingly isolated from the environment by a sterile connector such as a Lynx® ST or Lynx S2S valve available from Millipore Corporation. Alternatively they can have a hose barb and a plastic hose may extend from them that is sealed such as by clamps, Luer fittings, or a weldment at the end remote from the bag at which the port is attached (not shown). The tubes can be connected to other tubes by a tube welding device as is known in the industry.

Figure 2A:
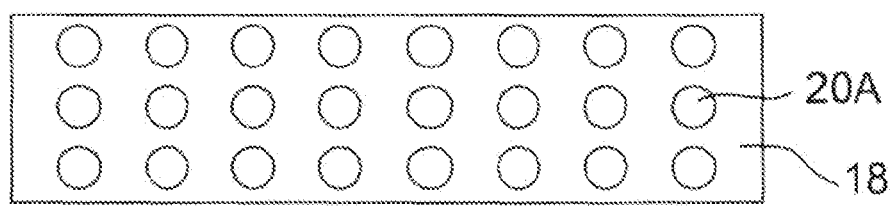
FIG. 2A shows a close up view of an alternative vortex breaker sheet of the present invention in cross-sectional view.
Figure 2B:
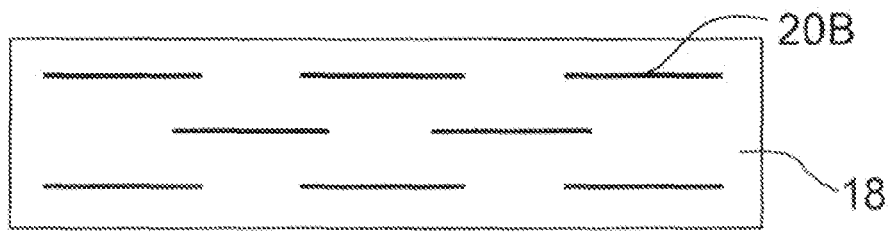
FIG. 2B shows a close up view of an alternative vortex breaker sheet of the present invention in cross-sectional view.

The bag 4 also contains a sheet 18 that extends between at least two of its inner surfaces such as the top 16, bottom 10 or side(s) 22. The sheet 18 may contain one or more perforations 20 that allow for fluid to circulate through the sheet to ensure good mixing. As shown in FIG. 1 the perforations 20 are a series of round openings that are arranged in alternating staggered rows of two and three openings. As shown in FIG. 2A, the perforations 20 may be arranged in parallel rows if desired. They may also be randomly distributed throughout the sheet 18 if desired. While shown as circular openings in these FIGS. 1 and 2A, they may be of other shapes such as triangles or polygons such as squares, rectangles, pentagons, and the like. Alternatively, the perforations 20 may be one or more slits 20B (as shown in FIG. 2B) formed in the sheet 18 and which open with the flow of the liquid in the mixer system 2.

As shown in the FIG. 1, the bag 4 has a generally cylindrical side wall 22 formed of one or more pieces of plastic film. This side wall 22 extends from the top 16 to the bottom 10.

The bottom 10 may be flat or tapered in a rounded or frusto-conical shape and its upper edge meets that of the side wall(s) 22 and its lower edge terminates either with the location of the mixing element if centrally located or with a port (not shown) if desired for removal of the fluid after mixing.

Figure 3:
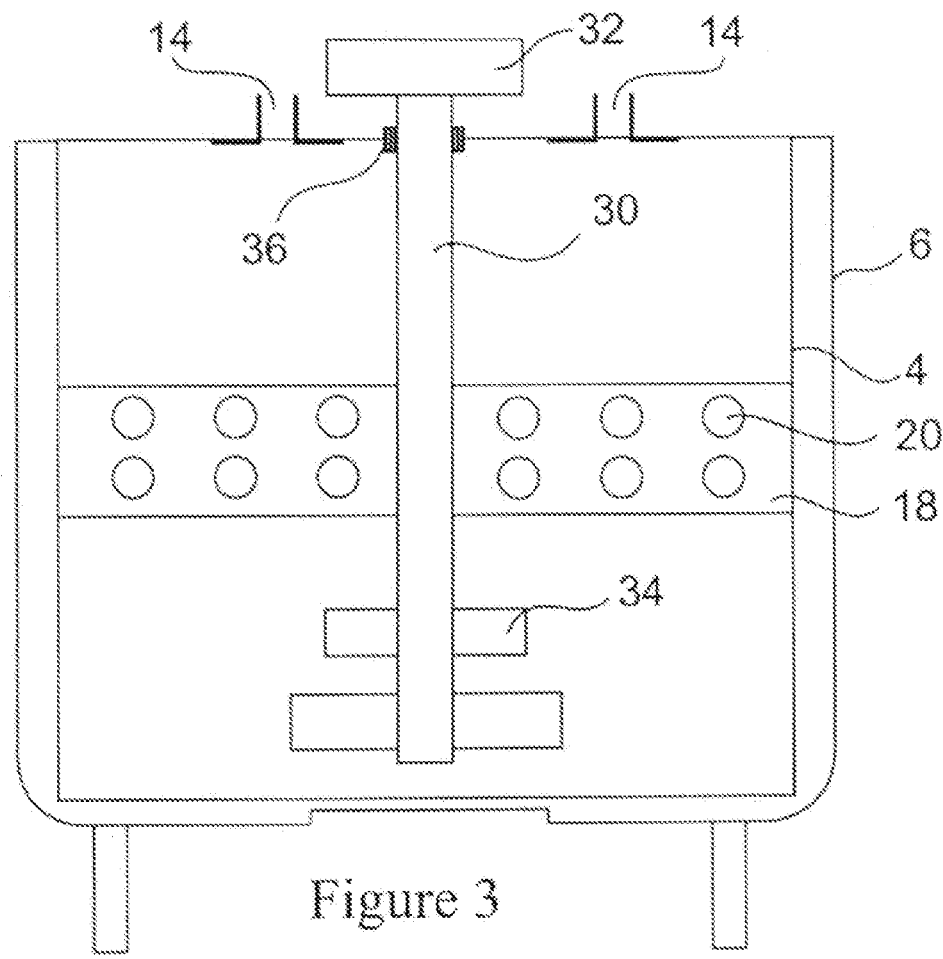
FIG. 3 shows a second embodiment of the present invention in cross-sectional view.
Figure 4:
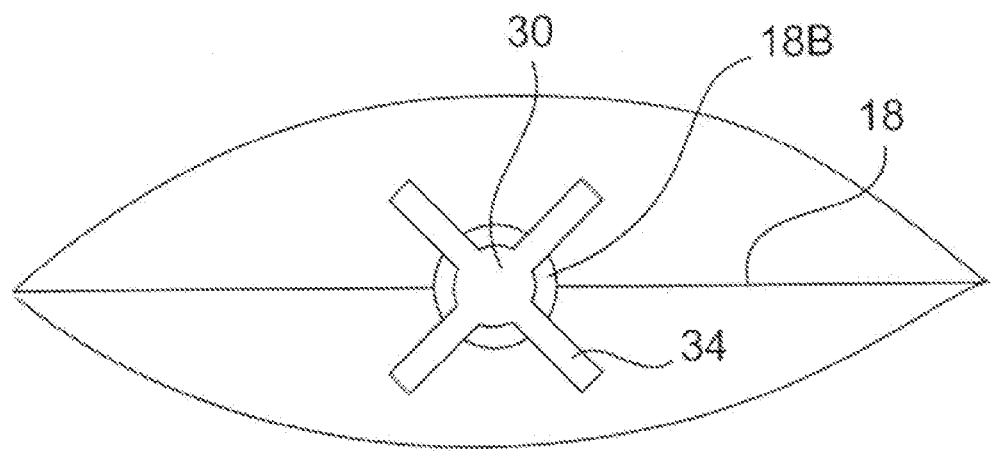
FIG. 4 shows the second embodiment of the present invention in top down cross-sectional view.

FIGS. 3 and 4 show an embodiment using a mixer that is driven by a shaft 30 from an external source such as motor or magnetic drive 32. The mixer has one or more impellers or blades 34 mounted to one or more sections of the shaft 30. While as shown the impellers 34 are on the lower portion of the shaft 30, they could also be located on an upper portion of the shaft as well or in lieu of the lower impellers 34 so long as one achieves the desired mixing without vortex formation. In FIG. 3, it can be seen that the bag 4 includes a fitting 36 that is attached to the to end of the bag 4. The fitting 36 may be attached by being ultrasonically welded, by adhesive or other attachment means. The fitting 36 may be of any suitable material, including plastic or metal. The fitting 36 supports lower bearings and upper bearings (not shown) as are known in the art such as by U.S. Pat. No. 7,547,135, which support the impeller shaft 30 for rotation. These bearings may be any suitable type of bearing including metal bearings or plastic bearings, but since they may come in contact with the fluid to be mixed are preferable selected to be dry running bearings.

At the top of the shaft 30 a drive system 32 such as an electric motor or magnetically coupled drive mechanism is provided to rotate the shaft 30.

The drive system 32 can be mounted onto the mixing assembly 2 via a bayonet bracket (not shown) that slides onto the outer surface of the fitting 36. The bayonet bracket has bearings that support the drive 32.

FIG. 4 shows a top down view of the embodiment of FIG. 3. In this instance the sheet 18 has an opening 18*b* formed through it in which the portion of the shaft 30 passes and rotates without touching the sheet 18. If desired this portion 18*b* of the sheet 18 maybe made of a rigid material or it may contain a rigid hollow tube such as a polycarbonate tube whose inner diameter is greater than that of the outer diameter of the shaft 30 that allows the shaft 30 to pass through and rotate within without touching the sheet 18.

Figure 5:
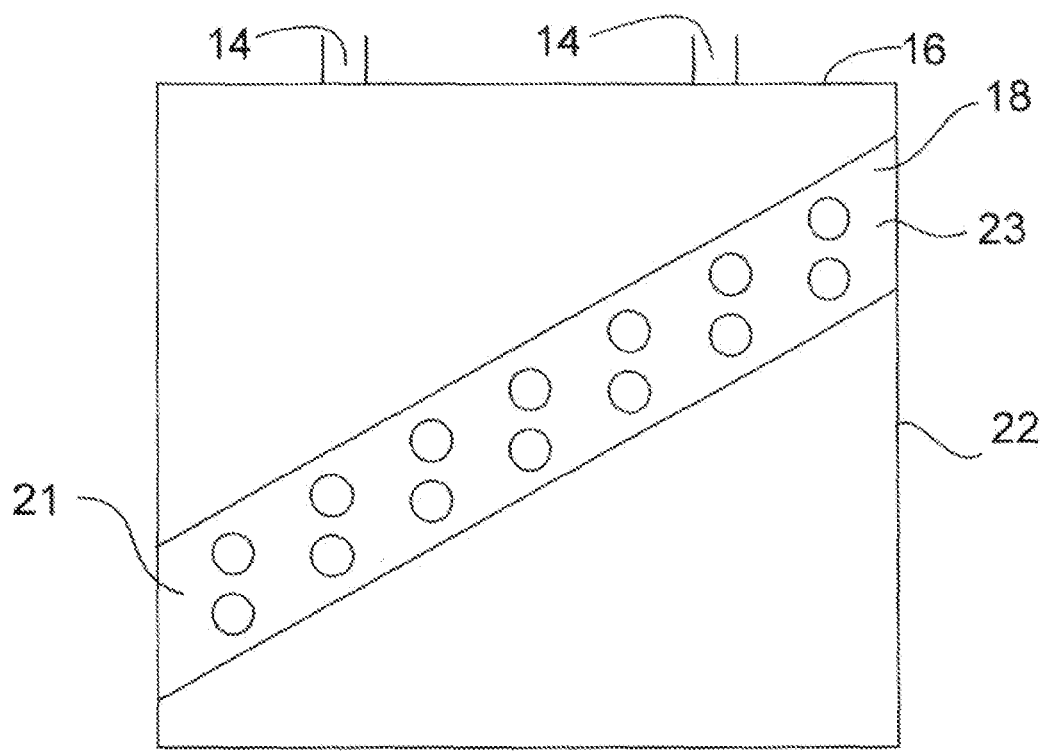
FIG. 5 shows an additional embodiment of the present invention in cross-sectional view.

FIG. 5 shows another embodiment of the sheet 18 as a vortex breaker in the mixing system 2. In this embodiment the sheet 18 is on a diagonal across the width of the bag 4 such that one end 21 of the sheet 18 is attached at a lower portion of the bag 4 than the other end 23 on the opposite side 22 or top 16.

Figure 6:
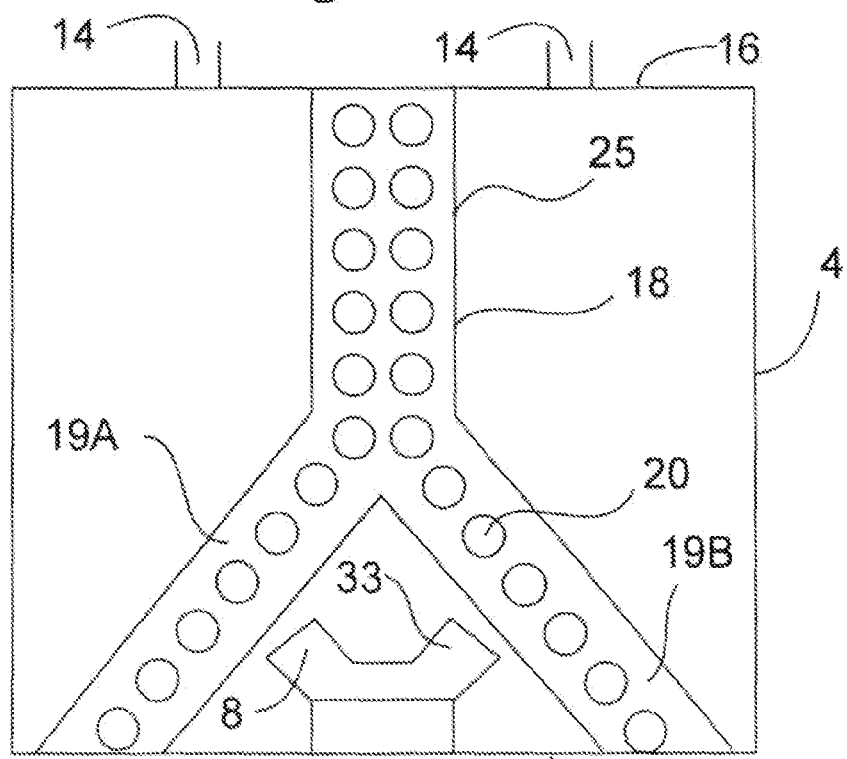
FIG. 6 shows another embodiment of the present invention in cross-sectional view.

FIG. 6 shows a further embodiment in which the sheet 18 is attached to the bottom 10 of the bag 4 by two legs 19A and B which converge and meet to form a substantially vertical portion 25. Preferably as shown the legs 19 A and B converge with the substantially vertical portion 25 over the drive 8 as shown or over the impellers 34 of the shaft drive system (not shown).

Figure 7A:
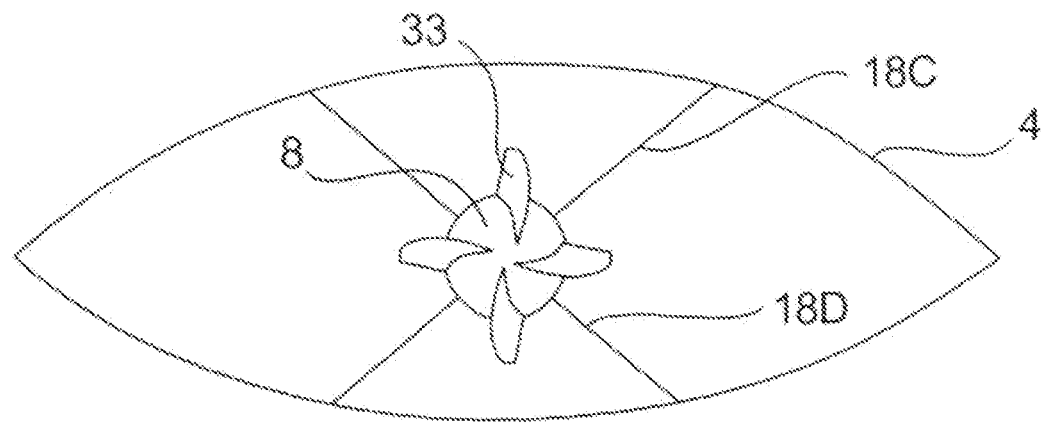
FIG. 7A shows a further embodiment of the present invention in top down cross-sectional view.
Figure 7B:
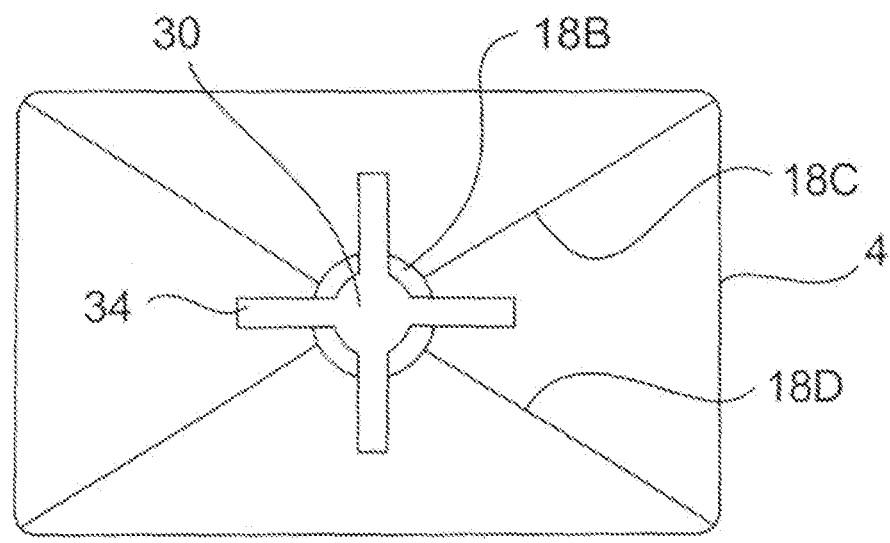
FIG. 7B shows a further embodiment of the present invention in top down cross-sectional view.

The vortex breaker sheet 18 may consist of more than one sheet such as is shown in FIGS. 7A and B. FIG. 7A shows a top down view of a two sheet device 18C and 18D with a bottom magnetic drive unit 8. FIG. 7B shows a top down view of a two sheet device 18C and 18D with a top shaft drive unit 30 and incorporating the opening 18B in the two sheets. While shown on a diagonal in both FIGS. 7A and B the sheets 18C and D do not need to be so and can meet each other at an angle from about 22.5 degrees to 135 degrees. Preferably they meet at an angle of between 30 to 120 degrees. More preferably they at meet at a 90 angle to each other.

Figure 8:
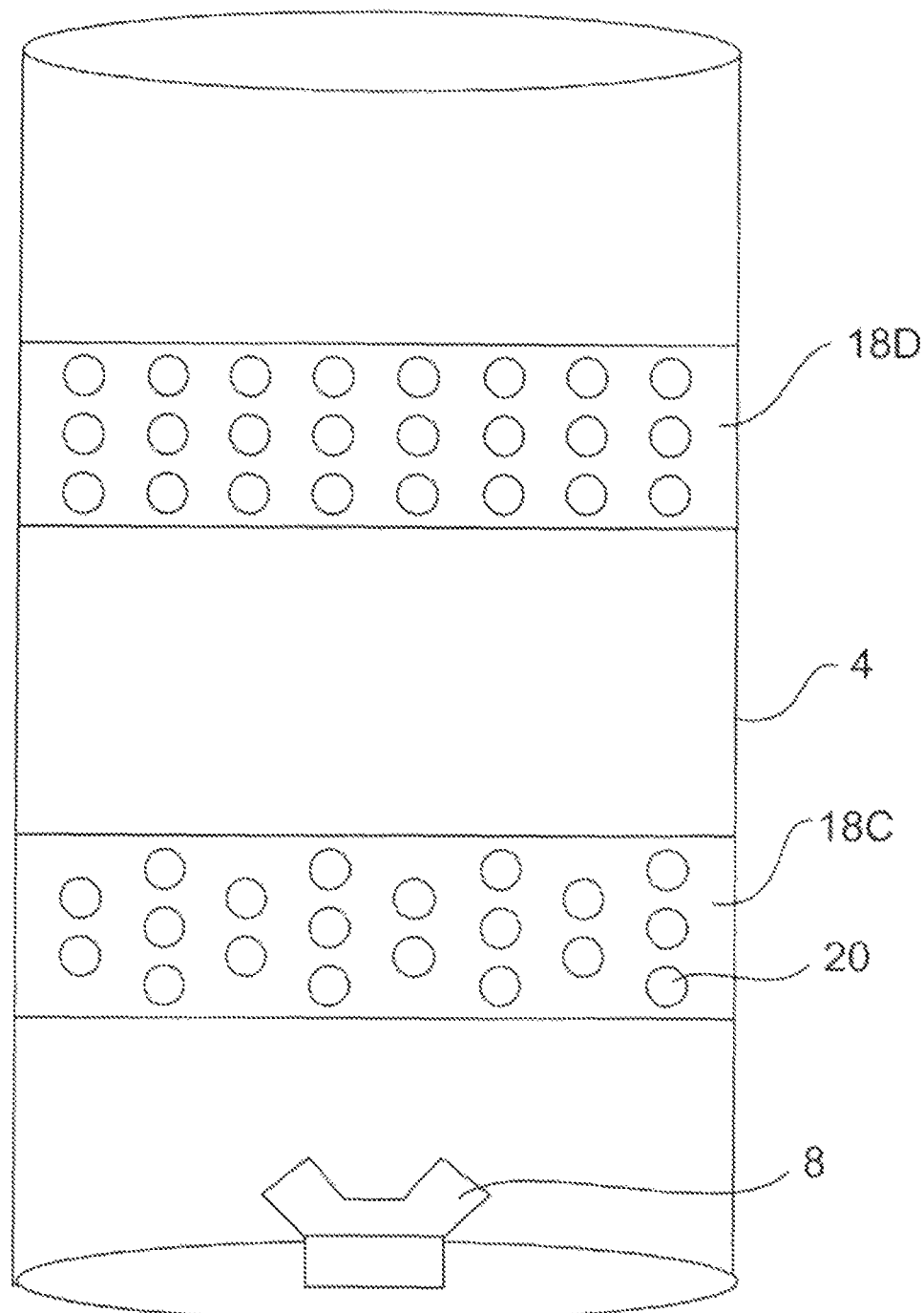
FIG. 8 shows a further embodiment of the present invention in cross-sectional view.

FIG. 8 shows another embodiment in which more than one or two or more sheets 18*c* and in this example are used and are spaced apart from each in a vertical manner. They may be parallel to each other or cross at an angle to each other as discussed above in regard to the embodiments of FIGS. 7A and B.

The sheet or sheets 18 can be arranged around (such as in FIG. 6) and /or above the bottom of the bag 4 as needed to achieve the desired vortex breaking effect. Generally it has been found that the vortex breaker (sheet 18) should be arranged above the mixing element as the vortex tends to occur above the impellers of the mixer device. The distance above the mixer device is one of design choice for the most part however it needs to small enough to interpret and /or prevent the vortex from forming. Generally the sheet(s) 18 should be at a height at least 5% of the height of the vertical sides of the bag above the impellers on the mixing device. The overall height of the sheet (s) 18 is not critical so long as it is sufficient to break the vortex formation as desired in the given bag and is of a height that does not interfere with the mixing of the components.

The sheet(s) 18 should either be flexible and capable of being stretched so that as the bag is inflated the sheet(s) become somewhat tight or taut. Alternatively, they can be of a length essentially equal to the width of the bag when inflated so that as the bag 4 expands the sheet 18 unfolds and becomes somewhat tight or taut. By somewhat tight or taut it is meant that the sheet 18 does not need to rigid or stretched tightly across the bag 4 in all circumstances. It may have some slack and may move slightly in the bag 4 so long as it is capable of remaining in the zone of vortex formation in order to prevent the vortex from forming.

The bag 4 of all the embodiments comprises a flexible and collapsible bag-like bag 4 having an interior surface and an exterior surface. Interior surface bounds a compartment or space into which liquid can be added. More specifically, bag 4 comprises a side wall 22 that, when bag 4 is unfolded, has a substantially circular or polygonal transverse cross section that extends between a first end and an opposing second end. First end terminates at a top end wall 16 while second end terminates at a bottom end wall 10.

Bag 4 is comprised of a flexible, water impermeable material such as polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The bag material comprises a single integral sheet which comprises two or more layer of different material separated by a contact layer that are either laminated together or all simultaneously co-extruded.

One example of an extruded material that can be used in the present invention is the Pureflex™ film and bags available from Millipore Corporation.

Another is the HyQ CX5-14 cast film available from HyClone Laboratories, Inc. This film comprises a polyester elastomer outer layer, an ultra-low density polyethylene contact layer, and an EVOH barrier layer disposed therebetween.

Another example of film that can be used is the Attane film which is also available from HyClone Laboratories, Inc. The Attane film is produced from three independent webs of blown film. The two inner webs are a 4 mil monolayer polyethylene film, while the outer barrier web is a 5.5 mil thick 6-layer coextrusion film.

In one embodiment, the material is approved for direct contact with living cells and is capable of maintaining a solution sterile. In such an embodiment, the material can also be sterilizable such as by ionizing radiation. Other examples of materials that can be used are disclosed in U.S. Pat. No. 6,083,587 which issued on Jul. 4, 2000 and U.S. patent application Ser. No. 10/044,636, filed Oct. 19, 2001 which are hereby incorporated by specific reference.

In one embodiment, bag 4 comprises a two-dimensional pillow style bag wherein two sheets of material are placed in overlapping relation and the two sheets are, bounded together at their peripheries to form internal compartment. Alternatively, a single sheet of material can be folded over and seamed around the periphery to form internal compartment. In the embodiment depicted, however, bag 4 comprises a three-dimensional bag which not only has a side wall(s) 22 but also a two dimensional top end wall 16 and a two dimensional bottom end wall 10.

Three dimensional bag 4 generally comprise a plurality, i.e., typically three or more, discrete panels. Often such bags are comprised of four panels, i.e., top panel, front side panel, back side panel and bottom panel. Each panel is sealed to the edges of the adjacent panels in a water tight manner by a seam. Panels are sealed together using methods known in the art such as heat energies, RF energies, sonics, other sealing energies, adhesives, or other conventional processes. It is appreciated that by altering the size and configuration of some or all of panels, bag 4 can be formed having a variety of different sizes and configurations. It is also appreciated that any number of panels can be used to adjust the size and configuration of bag 4.

In still other embodiments, it is appreciated that bag 4 can be formed by initially extruding or otherwise forming a polymeric sheet in the form of a continuous tube. In one embodiment, the tube can simply be cut to length and each end seamed closed to form a two-dimensional pillow style bag. In an alternative embodiment, each end can be folded like the end of paper bag and then seamed closed so as to form a three dimension body. In still another embodiment, a length of tube can be laid flat so as to form two opposing folded edges. The two folded edges are then inverted inward so as to form a pleat on each side. The opposing end of the tube are then seamed closed. Finally, an angled seam is formed across each corner so as to form a three dimensional bag when inflated.

It is appreciated that the above techniques can be mixed and matched with one or more polymeric sheets and that there are still a variety of other ways in which bag 4 can be formed having a two or three dimensional configuration. Such bags and their manufacture are well known and widely available.

It is appreciated that bag 4 can be manufactured to have virtually any desired size, shape, and configuration. For example, bag 4 can be formed to hold 50 liters, 100 liters, 200 liters, or other desired amounts. Although bag 4 can have a substantially box shaped configuration, bag 4, as depicted in the Figures, conforms to the configuration of the container 6 as it is filled with solution. In one embodiment, however, bag 4 can be specifically configured to be complementary or substantially complementary to the container 6.

In any embodiment, however, it is desirable that when bag 4 is received within the container 6 it is uniformly supported by floor and side walls of container 6. Having at least generally uniform support of bag 4 by container 6 helps to preclude failure of the bag 4 by hydraulic forces applied to the bag 4 when filled with a solution.

A device according to the invention can be made in many ways. In either a two dimensional or three dimensional bag, one simply incorporates and aligns each end of the vortex breaking sheet with a seam to be formed and uses the manufacturing effort of forming the seam such as by heat or glue to attach the end of the sheet into the seam of the bag. Other means such as attaching the ends after bag formation may also be used however they are not as convenient as including the sheet(s) during manufacture.

One can also simply create a tab on the desired seams that extends into the space of the bag 4 and attach the vortex breaking sheet(s) to 18 to the tabs such as by welding, adhesives or mechanical fasteners such as rivets.

In use, the bag 4 is generally retained with a holder or carrier 6 such as a plastic or metal vat or tank. The bag 4 may be inflated with some air or gas before liquid is added if desired. As the bag is 4 filled the sheet 18 simply expands and conforms to the space with the movement of the bag 4. When the mixing device 8, be it a bottom mount or top mount design, is turned on, the sheet 18 occupies at least a portion of the space in which a vortex is normally formed thus disrupting its formation and allowing the mixer to mix without a vortex.

If needed, one can first make a bag 4 without the vortex breaking sheet 18 and determine where the vortex is forming. Then one can build a bag 4 with the vortex breaking sheet(s) 18 located at least partially within the Zone of the vortex so as to disrupt the vortex formation for that type and size of bag 4.

EXAMPLE

A single use mixer system, Mobius® mixer 100 system available from Millipore Corporation, was used in this example. The bag and the vortex breaking sheet were made of Pureflex™ film, available from Millipore Corporation. The mixer was a Levitronix magnetic mixer with a plastic impeller and magnetic element contained within the bag and a magnetic drive unit located outside the bag below the impeller and coupled to the impeller by magnetic forces to cause the impeller to rotate.

A first (Control) bag was used with no vortex breaker. The motor was run at 560 revolutions per minute (RPM) and a sustained vortex was formed above the impeller blades in about 3 seconds after starting the motor and remained until the motor power was shut off.

A second (Invention) bag was modified by taking a sheet of Pureflex film approximately ten inches in height and extending it across the width of the bag and heat sealing it to the inner seams formed on each side of the bag. Three parallel rows (horizontal) of two inch holes were made by a hand punch to the sheet. There were approximately six holes per row. The motor was run at 560 revolutions per minute (RPM) and no vortex was formed above the impeller blades.

What we claim:

1. A disposable mixer comprising a plastic bag having an internal volume defined by the inner surfaces of the bag, a disposable mixing element contained within the internal volume of the bag and a vortex breaker formed of one or more sheets of plastic material, each sheet of the vortex breaker having a first end and a second end, the first end being attached to a first inner surface of the bag and the second end being attached to a second inner surface of the bag which is at different location in the bag from the first inner surface with the one more sheets of the vortex breaker extending between the first and second inner surfaces of the bag.

2. The mixer of claim 1 wherein the one or more sheets of the vortex breaker extend from a first side of the bag forming the first inner surface of the bag to a second side of the bag forming the second inner surface of the bag.

3. The mixer of claim 1 wherein the one or more sheets of the vortex breaker contain one or more openings in each sheet of the vortex breaker.

4. The mixer of claim 1 wherein the one or more sheets of the vortex breaker extend from a bottom of the bag forming the first inner surface of the bag to a top of the bag forming the second inner surface of the bag.

5. The mixer of claim 1 wherein the one or more sheets of the vortex breaker extend from a first side of the bag forming the first inner surface of the bag to a second side of the bag forming the second inner surface of the bag and each sheet contains one or more openings in each sheet of the vortex breaker.

6. The mixer of claim 1 wherein the one or more sheets of the vortex breaker extend from a bottom of the bag forming the first inner surface of the bag to a top of the bag forming the second inner surface of the bag.

7. The mixer of claim 1 wherein the one or more sheets of the vortex breaker extend from a bottom of the bag forming the first inner surface of the bag to a top of the bag forming the second inner surface of the bag and each sheet of the vortex breaker contains one or more openings.

8. The mixer of claim 1 wherein the mixing element is selected from the group consisting of magnetic stir bars and magnetically driven mixers.

9. The mixer of claim 1 wherein the mixing element is selected from the group consisting of magnetic stir bars and magnetically driven mixers and the mixing element is driven by a magnetically driver mixer located outside of the bag for rotating the mixing element.

10. The mixer of claim 1 wherein the bag is a two-dimensional pillow style bag formed of a single bag sheet of material that is folded over and seamed around a periphery of the folded bag sheet to form an internal compartment.

11. The mixer of claim 1 wherein the bag is a two-dimensional pillow style bag formed of two bag sheets of material are placed in overlapping relation and the bag two sheets are bounded together at their peripheries to form an internal compartment.

12. A disposable mixer comprising a plastic bag having an internal volume defined by the inner surfaces of the bag, wherein the bag is a two-dimensional pillow style bag, the bag having a top inner surface and a bottom inner surface, a magnetically driven disposable mixer mounted to the bottom of the bag and contained within the internal volume of the bag and one or more sheets of plastic material forming a vortex breaker attached to the top inner surface of the bag and extending to and being attached to the bottom inner surface of the bag.

13. The mixer of claim 12 wherein each of the one or more sheets of the vortex breaker contains one or more openings.

14. The mixer of claim 12 wherein the bag contains two or more sheets of the vortex breaker formed on either side of the magnetically driven disposable mixer mounted to the bottom of the bag.

15. The mixer of claim 12 wherein the bag is a two-dimensional pillow style bag formed of two bag sheets of material are placed in overlapping relation and the two bag sheets are bounded together at their peripheries to form an internal compartment.

16. The mixer of claim 12 wherein the bag is a two-dimensional pillow style bag formed of a single bag sheet of material that is folded over and seamed around a periphery of the folded bag sheet periphery to form an internal compartment.

17. The mixer of claim 12 wherein the mixing element is driven by a drive mechanism located outside of the bag for rotating the mixing element.

* * * * *

UNITED STATES PATENT AND TRADEMARK OFFICE
CERTIFICATE OF CORRECTION

Page 1 of 1

PATENT NO. : 8,556,497 B2
APPLICATION NO. : 13/399354
DATED : October 15, 2013
INVENTOR(S) : Martin Morrissey et al.

It is certified that error appears in the above-identified patent and that said Letters Patent is hereby corrected as shown below:

On title page, in column 1, below item (65) insert -- Related U.S. Application Data (62) Division of application No. 13/178,097, filed on Jul. 7, 2011. (60) Provisional application No. 61/369,249, filed on Jul. 30, 2010. --, therefor.

In the Claims

Column 8, line 62, in claim 1 delete "one more" and insert -- one or more --, therefor.

Column 9, line 29, in claim 9 delete "driver" and insert -- driven --, therefor.

Column 10, line 3, in claim 11 delete "are," therefor.

Column 10, line 24, in claim 15 delete "are," therefor.

Signed and Sealed this
Sixteenth Day of September, 2014

Michelle K. Lee
*Deputy Director of the United States Patent and Trademark Office*